(12) United States Patent
Avery et al.

(10) Patent No.: US 9,649,447 B2
(45) Date of Patent: *May 16, 2017

(54) FLEXIBLE FASTENER FOR DRUG DELIVERY DEVICE

(75) Inventors: Richard James Vincent Avery, Gloucestershire (GB); Aled Meredydd James, Dorridge (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/825,141

(22) PCT Filed: Sep. 28, 2011

(86) PCT No.: PCT/EP2011/066929
§ 371 (c)(1),
(2), (4) Date: Mar. 20, 2013

(87) PCT Pub. No.: WO2012/041931
PCT Pub. Date: Apr. 5, 2012

(65) Prior Publication Data
US 2013/0184651 A1    Jul. 18, 2013

Related U.S. Application Data

(60) Provisional application No. 61/388,036, filed on Sep. 30, 2010.

(30) Foreign Application Priority Data

Dec. 13, 2010   (EP) .................................... 10194723

(51) Int. Cl.
*A61M 5/31*     (2006.01)
*A61M 5/315*    (2006.01)
(Continued)

(52) U.S. Cl.
CPC .......... *A61M 5/31545* (2013.01); *A61M 5/24* (2013.01); *A61M 5/3135* (2013.01);
(Continued)

(58) Field of Classification Search
CPC .. A61M 5/24; A61M 5/3158; A61M 5/31595; A61M 5/31551; A61M 39/045;
(Continued)

(56) References Cited

U.S. PATENT DOCUMENTS 4,376,525 A    3/1983 Fremy
8,968,257 B2   3/2015 Dasbach et al.
(Continued)

FOREIGN PATENT DOCUMENTS

EP    0023853       2/1981
JP    2009-543631   12/2009
(Continued)

OTHER PUBLICATIONS

International Search Report for Int. App. No. PCT/EP2011/066929, completed Oct. 14, 2011.
(Continued)

*Primary Examiner* — Imani Hayman
(74) *Attorney, Agent, or Firm* — McDonnell Boehnen Hulbert & Berghoff LLP (57) ABSTRACT

An assembly is presented having a reservoir holder, a dose setting mechanism, and flexible fastener configured to fasten the reservoir holder to the dose setting mechanism, wherein the flexible fastener is provided at one of the reservoir holder and the dose setting mechanism. The flexible fastener is configured to releasably fasten the reservoir holder and the dose setting mechanism to each other. Moreover, said flexible fastener is arranged on a retention ring provided at the
(Continued)

one of the reservoir holder and the dose setting mechanism. Furthermore, a drug delivery device with such an assembly is disclosed.

10 Claims, 9 Drawing Sheets

(51) Int. Cl.
 *A61M 5/24* (2006.01)
 *A61M 39/10* (2006.01)
(52) U.S. Cl.
 CPC ..... *A61M 5/31511* (2013.01); *A61M 5/31551* (2013.01); *A61M 2005/2492* (2013.01); *A61M 2039/1066* (2013.01)
(58) Field of Classification Search
 CPC .......... A61M 39/14; A61M 2005/2407; A61M 2005/2433; A61M 2005/2488; A61M 5/3135; A61M 5/31545; A61M 2005/2403; A61M 2005/2492; A61M 2039/1066; A61M 5/31511; G06C 27/00
 USPC ................. 604/207, 208, 209, 210, 211, 246
 See application file for complete search history.

(56) References Cited

U.S. PATENT DOCUMENTS

2002/0149200 A1 10/2002 Fumioka
2009/0259197 A1* 10/2009 Christiansen ................. 604/208
2010/0030158 A1* 2/2010 Christiansen ................. 604/208

FOREIGN PATENT DOCUMENTS

WO 2005/018721 3/2005
WO 2006/036192 4/2006

OTHER PUBLICATIONS

European Search Report for EP Application No. 10194723.2, dated Jun. 17, 2011.
International Search Report and Written Opinion for Int. App. No. PCT/EP2011/066929, mailed Oct. 21, 2011.
Japanese Office Action for JP Application No. 2013-530722, mailed Jul. 28, 2015.

* cited by examiner

FLEXIBLE FASTENER FOR DRUG DELIVERY DEVICE

CROSS REFERENCE TO RELATED APPLICATIONS

The present application is a U.S. National Phase Application pursuant to 35 U.S.C. §371 of International Application No. PCT/EP2011/066929 filed Sep. 28, 2011, which claims priority to U.S. Provisional Patent Application No. 61/388,036 filed Sep. 30, 2010 and European Patent Application No. 10194723.2 filed Dec. 13, 2010. The entire disclosure contents of these applications are herewith incorporated by reference into the present application.

FIELD OF DISCLOSURE

The present disclosure is generally directed to medical delivery devices and to reservoirs, particularly reservoirs containing a medicament that may be used with a medical delivery device. More particularly, the present disclosure is generally directed to features of a reservoir, a reservoir holder and/or a medical delivery device so as to enable easy mounting of the reservoir or reservoir holder on the medical delivery device and to prevent unwanted reservoir tampering and/or reservoir inadvertent cross use. As just one example, such medicament reservoirs may comprise an ampoule, a cartridge, a vial, or a pouch, and may be used with a medical delivery device. Exemplary medical delivery devices include, but are not limited to syringes, pen type injection devices, pen type injection syringes, pumps, inhalers, or other similar injection or infusing devices that utilize at least one reservoir containing at least one medicament, drug or medication.

BACKGROUND

Medicament reservoirs such as ampoules, cartridges, or vials are generally known. Such reservoirs are especially used for medicaments that may be self administered by a patient. For example, with respect to insulin, a patient suffering from diabetes may require a certain amount of insulin to either be injected via a pen type injection syringe or infused via a pump. With respect to certain known reusable pen type drug delivery devices, a patient may load a reservoir containing the insulin into a proximal end of a reservoir holder. After the reservoir has been correctly loaded, the user may then select or may be called upon to select a dose of the medicament. Multiple doses may be dosed from the reservoir. The doses may be fixed or varied by the user, i.e. the amount of the medicament expelled during an injection may be fixed or variable. The medical delivery device, i.e. the drug delivery device may be a disposable device or a reusable device. Where the drug delivery device comprises a reusable device, once the reservoir is empty, the reservoir holder is disconnected from the drug delivery device and the empty reservoir is removed and replaced with a new filled reservoir. Most suppliers of such reservoirs recommend that the user disposes of the empty reservoirs properly. Alternatively, where the drug delivery device comprises a disposable device, once the reservoir is empty, the user is recommended to dispose of the entire device and obtain a new device having a properly filled reservoir.

Such known self administration systems, especially reusable systems requiring the removal of empty reservoirs and reloading of filled reservoirs, have certain limitations. For example, in certain generally known systems, a user may simply remove a reservoir and load a new reservoir into the delivery system without the drug delivery device or without the reservoir or reservoir holder having any mechanism of preventing unintentional removal of a reservoir and/or subsequent cross use of an incorrect reservoir. In particular, patients with limited manual dexterity may cause unintentional removal of a reservoir during use of the device. This may result in malfunction of the device and/or unnecessary puzzlement of the patients.

Furthermore, certain known drug delivery devices do not present any mechanism for determining if the correct type of medicament within the reservoir should be used with that particular drug delivery system. This potential problem could be exacerbated given that certain elderly patients, such as those suffering from diabetes, may have limited manual dexterity. Identifying an incorrect medicament is quite important, since the administration of an incorrect medicament or the administration of a potentially incorrect dose of a medicament such as a short acting insulin in lieu of a long acting insulin or an incorrect amount of insulin could result in injury or even death.

Some drug delivery devices or systems may use a color coding scheme to assist a user or care giver in selecting the correct reservoir to be used with a drug delivery device. However, such color coding schemes pose challenges to certain users, especially those users suffering from poor eyesight or color blindness: a situation that can be quite prevalent in patients suffering from diabetes.

Another concern that may arise with such disposable reservoirs is that these reservoirs are manufactured in essentially standard sizes and must comply with certain recognized local and international standards. Consequently, such reservoirs are typically supplied in standard sized reservoirs (e.g., 3 ml reservoirs). Therefore, there may be a variety of reservoirs supplied by a number of different suppliers and containing different medicaments but which may fit a single drug delivery device. As just one example, a first reservoir containing a first medicament from a first supplier may fit a medical delivery device provided by a second supplier. As such, a user might inadvertently load and then dispense an incorrect medicament (such as a rapid or basal type of insulin) into a drug delivery device without being aware that the drug delivery device was perhaps neither designed nor intended to be used with such a reservoir and/or such a type of medicament.

As such, there is a growing desire from users, health care providers, care givers, regulatory entities, and medical device suppliers to reduce the potential risk of a user unintentionally removing a reservoir and/or loading a reservoir with an incorrect drug type into a drug delivery device. There is also, therefore, a desire to reduce the risk of dispensing an incorrect medicament or a wrong concentration of a medicament from such a drug delivery device.

There is, therefore, a general need to physically dedicate a reservoir to its medication or drug type and design a medication delivery device that enables easy mounting and removal of a reservoir or reservoir holder and nevertheless prevents unwanted reservoir cross use and/or unintentional removal of the reservoir or reservoir holder.

There is also a general need to provide a dedicated reservoir and/or a dedicated reservoir holder that is difficult to tamper with so that the reservoir may not be compromised in that the reservoir can be used with an unauthorized drug or drug delivery device. Because such reservoirs or reservoir holders may be difficult to tamper with, they may also reduce the risk of counterfeiting: i.e., making it more difficult for counterfeiters to provide unregulated counterfeit medicament carrying products.

Therefore, the general problem to be solved by the present disclosure is to provide a reservoir, a reservoir holder and a drug delivery system which facilitate an administration of reservoirs and/or reservoir holders.

SUMMARY

An assembly is disclosed comprising a reservoir holder, a dose setting mechanism and a flexible fastener configured to fasten the reservoir holder to the dose setting mechanism. The flexible fastener is provided at one of the reservoir holder and the dose setting mechanism. The dose setting mechanism may be a part of a medical or drug delivery device. The dose setting mechanism may be configured such that a predetermined dose of a medicament may be set. Moreover, the dose setting mechanism may be configured such that a predetermined dose of a medicament may be dispensed via dispensing means connected to or being part of the dose setting mechanism. Therefore, the dose setting mechanism may have dose setting functionality as well as dose dispensing functionality. It is conceivable that a reservoir instead of a reservoir holder is provided with a flexible fastener of the kind explained above. Then the reservoir may directly be connected and fastened to the dose setting mechanism. The assembly may comprise only one of the reservoir, reservoir holder, and the dose setting mechanism. The reservoir may be contained within the reservoir holder. The reservoir may for example be any kind of a cartridge and may contain any kind of medicament, medication or drug.

The flexible fastener may be arranged on a retention ring or fastening ring provided at the one of the reservoir holder and the dose setting mechanism. The reservoir holder or the dose setting mechanism may be connected or disconnected to or from each other by radially bending the retention ring such that the flexible fastener is brought into or out of engagement with corresponding engagement means on the corresponding other one of the reservoir holder or dose setting mechanism.

The flexible fastener may comprise at least one flexible arm bendable for connecting or disconnecting the reservoir holder with or from the dose setting mechanism. This allows for a simple but effective fastening or disengaging of the reservoir holder to or from the dose setting mechanism. The flexible fastening may aid a patient, especially one with limited manual dexterity, to simply fasten the parts to each other.

The flexible fastener of the one of the reservoir holder and the dose setting mechanism may comprise at least one protrusion for engaging at least one aperture provided near a distal end of the other one of the reservoir holder and the dose setting mechanism. This means, the flexible fastener of the reservoir holder may comprise at least one protrusion for engaging at least one aperture provided near a distal end of the dose setting mechanism. Alternatively the flexible fastener of the dose setting mechanism may comprise at least one protrusion for engaging at least one aperture provided near a proximal end of the reservoir or the reservoir holder. The aperture therefore may have the function of an engagement means for engaging with a corresponding protrusion of a flexible fastener.

The retention ring may for example comprise a plurality of radial protrusions. The radial protrusions may extend toward the center of the fastening ring. The retention ring may comprise a circular shape or other various shapes and sizes to vary assembly and disassembly forces required by a user. Moreover, the retention ring may be made from a flexible material. In alternative embodiments, the retention ring may be split or may comprise more than one component part.

Preferably, the retention ring is radially bendable in such a way that the flexible fastener, e.g. radial protrusions of the retention ring, may describe a movement in radial direction, i.e. perpendicular to the main axis of the assembly, into or out of an engagement with respective engagement means, e.g. openings or grooves on the other one of the reservoir holder and the dose setting mechanism.

The flexible fastener may provide a differentiation feature for coding the reservoir holder or the dose setting mechanism. This may aid a patient to prevent unwanted cross use of a reservoir or reservoir holder in connection with a dose setting mechanism. Moreover, this may aid to prevent loading a reservoir with an incorrect drug type into a drug delivery device. The differentiation feature or coding feature may be provided by a characterising shape of at least a part of the flexible fastener, e.g. the shape of a protrusion or a flexible arm. But it is also conceivable that the differentiation feature or coding feature may be provided as a part separated from the flexible fastener.

The assembly may comprise a sleeve configured to be axially movable and to interact with the flexible fastener for connecting or disconnecting the reservoir holder with or from the dose setting mechanism. The sleeve may be movable from a first axial position to a second axial position so as to prevent the reservoir holder to be disconnected from said dose setting mechanism in the first axial position of the sleeve and to allow the reservoir holder to be disconnected from said dose setting mechanism in the second axial position of the sleeve. This may prevent unwanted or unintentional removal of the reservoir holder, and consequently of a reservoir contained within the reservoir holder, from the dose setting mechanism of a drug delivery device or system during use. In particular, patients with limited manual dexterity are given more safety in handling the system.

According to one embodiment the sleeve may conceal at least a portion of said flexible fastener when the reservoir holder is connected to the dose setting mechanism. This may aid in prevent unintentional removal of the reservoir holder from the dose setting mechanism, since the flexible fastener may be inhibited in disconnecting from the reservoir holder or dose setting mechanism respectively.

The reservoir holder may comprise a tubular member, said tubular member extending from a distal end to a proximal end of said reservoir holder. A first coupling mechanism may be provided at said distal end of said tubular member, said first coupling mechanism being configured for releasably coupling a dispense interface to the reservoir holder. Such a dispense interface may be for example a needle assembly or other kind of dispense assembly for bringing a drug or medication out of a device and into or onto a human body.

A drug delivery device of the kind mentioned above may comprise an assembly as explained above, a dose setting means for setting a dose of a drug to be dispensed, and a piston rod, wherein after said dose has been set, said piston rod can be rotated to dispense said dose. The dose setting means may be part of or separated from the dose setting mechanism of the assembly.

According to an exemplary arrangement, a reservoir assembly is disclosed. The reservoir assembly comprises a reservoir holder comprising a tubular member. The tubular member extends from a distal end to a proximal end of said reservoir holder. A first coupling mechanism is provided at the distal end of said tubular member. The first coupling mechanism is configured for releasably coupling a dispense interface. A flexible fastener is provided near the proximal end of the tubular member such that the flexible fastener is configured to releasably fasten the reservoir holder to a dose setting mechanism.

According to another exemplary arrangement, a dose setting mechanism is disclosed. The dose setting mechanism comprises an outer housing. The outer housing extends from a distal end of the dose setting mechanism to a proximal end of the dose setting mechanism. A dose setter is provided at the proximal end of the dose setting mechanism. A flexible fastener is provided near the distal end of the housing of the dose setting mechanism such that the flexible fastener is configured to releasably fasten the dose setting mechanism to a reservoir holder.

The terms "medicament", "medication" or "drug" as used throughout this disclosure, mean a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, a antibody, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

In the following text, a set of particularly advantageous aspects is specified. Within the set, numbers are used to identify specific aspects. This facilitates referencing the features of specific aspects in other aspects.

1. A reservoir assembly comprising:
a reservoir holder comprising a tubular member, said tubular member extending from a distal end to a proximal end of said reservoir holder;
a first coupling mechanism provided at said distal end of said tubular member, said first coupling mechanism configured for releasably coupling a dispense interface; and
a flexible fastener provided near said proximal end of said tubular member;
such that said flexible fastener is configured to releasably fasten said reservoir holder to a dose setting mechanism.

2. The reservoir assembly of aspect 1 wherein said flexible fastener comprises a plurality of flexible features.

3. The reservoir assembly of aspect 2 wherein said plurality of flexible features comprise a plurality of flexible arms.

4. The reservoir assembly of aspect 2 wherein said plurality of flexible features are configured to engage at least one aperture provided near a distal end of a dose setting mechanism.

5. The reservoir assembly of aspect 1 wherein said tubular member of said reservoir holder defines an inner cavity that is dimensioned to receive a reservoir containing a medicament.

6. The reservoir assembly of aspect 5 wherein said reservoir assembly is releasably coupled to a dose setting mechanism and
wherein said dose setting mechanism comprises a dose setter such that said dose setter can be rotated so as to allow a user of said dose setting mechanism to select a dose of said medicament contained in said reservoir.

7. The reservoir assembly of aspect 1 wherein said reservoir assembly is configured to releasably retain a removable cap.

8. The reservoir assembly of aspect 1 further comprising a sleeve that moves axially over a portion of said reservoir assembly and a portion of said dose mechanism when said reservoir assembly is connected to a dose setting mechanism.

9. The reservoir assembly of aspect 8 wherein said sleeve conceals at least a portion of said flexible fastener when said reservoir assembly is connected to said dose setting mechanism.

10. The reservoir assembly of aspect 9 wherein said sleeve is configured such that said sleeve can be moved from a first position to a second position so as to allow said reservoir assembly to be disconnected from said dose setting mechanism.

11. The reservoir assembly of aspect 1 wherein said reservoir assembly comprises a molded reservoir assembly.

12. A dose setting mechanism comprising:
an outer housing, said outer housing extending from a distal end of said dose setting mechanism to a proximal end of said dose setting mechanism;
a dose setter provided at said proximal end of said dose setting mechanism;
a flexible fastener provided near said distal end of said housing of said dose setting mechanism;
such that said flexible fastener is configured to releasably fasten said dose setting mechanism to a reservoir holder.

13. The dose setting mechanism of aspect 12 wherein said flexible fastener comprises a plurality of flexible features.

14. The dose setting mechanism of aspect 13 wherein said plurality of flexible features comprise a plurality of flexible arms.

15. The dose setting mechanism of aspect 14 wherein said plurality of flexible arms are configured to engage at least one aperture provided near a proximal end of a reservoir holder.

16. The dose setting mechanism of aspect 12 wherein said flexible fastener comprises a retention ring, wherein said retention ring is configured to secure said reservoir holder to said dose setting mechanism.

17. The dose setting mechanism of aspect 16 wherein said retention ring comprises at least one fastening arm configured to engage a corresponding groove of said reservoir holder so as to retain said reservoir holder to said dose setting mechanism.

18. The dose setting mechanism of aspect 16 further comprising a sleeve that moves axially over a portion of said reservoir assembly and a portion of said dose mechanism when said reservoir assembly is connected to a dose setting mechanism.

19. The dose setting mechanism of aspect 18 wherein said sleeve conceals at least a portion of said retention ring when said reservoir assembly is connected to said dose setting mechanism.

20. The dose setting mechanism of aspect 19 wherein said sleeve is configured such that said sleeve can be moved from a first position to a second position so as to allow said reservoir assembly to be disconnected from said dose setting mechanism.

21. The dose setting mechanism of aspect 12 wherein said flexible fastener comprises a fastening ring.

22. The drug delivery system of aspect 18 wherein said fastening ring comprises a split fastening ring.

23. The dose setting mechanism of aspect 18 wherein said fastening ring comprises at least one protrusion configured to engage a corresponding groove of said reservoir holder so as to retain said reservoir holder to said dose setting mechanism.

24. The dose setting mechanism of aspect 20 further comprising a sleeve that moves axially over a portion of a reservoir assembly and a portion of said dose mechanism when said reservoir assembly is connected to a dose setting mechanism.

25. The dose setting mechanism of aspect 20 wherein said sleeve conceals at least a portion of said flexible fastener when a reservoir assembly is connected to said dose setting mechanism.

26. The dose setting mechanism of aspect 20 wherein said sleeve is configured such that said sleeve can be moved from a first position to a second position so as to allow a reservoir assembly to be disconnected from said dose setting mechanism.

27. The dose setting mechanism of aspect 16 further comprising a spindle,
wherein after said dose setter has been rotated to select a dose of medicament contained within said reservoir holder, said spindle can be rotated to dispense said selected dose.

Features described herein-above and below in conjunction with different aspects, embodiments, arrangements etc., may, of course, be combined with each other. Instead of the reservoir holder, a reservoir may directly be provided with the flexible fastener as explained above.

These as well as other advantages of various aspects of the present disclosure will become apparent to those of ordinary skill in the art by reading the following detailed description, with appropriate reference to the accompanying drawings.

BRIEF DESCRIPTION OF THE DRAWINGS

Exemplary embodiments are described herein with reference to the drawings, in which.

DETAILED DESCRIPTION

Figure 1:
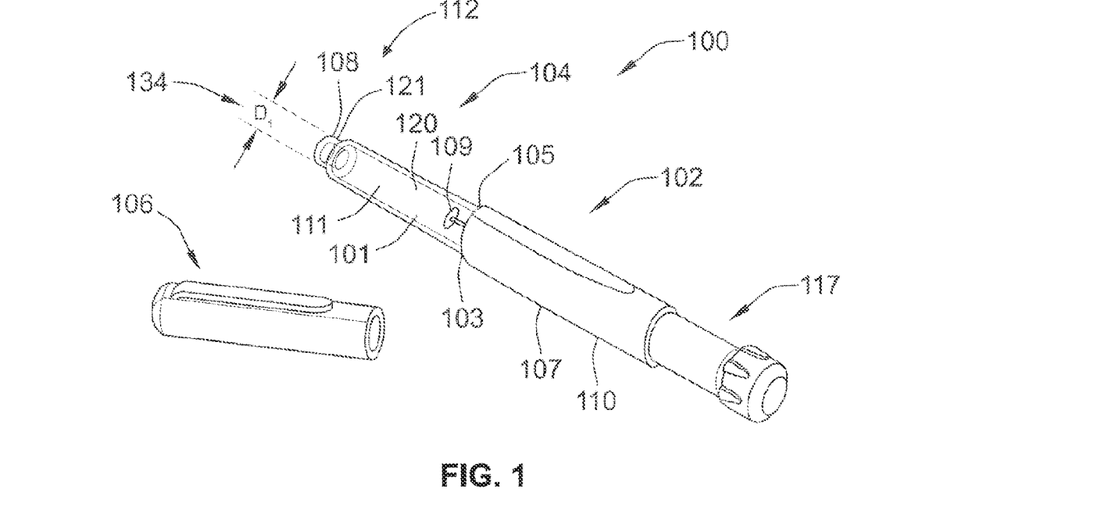
FIG. 1 illustrates an exemplary pen type drug delivery device.

Referring to FIG. 1, there is shown a drug delivery device 100 in the form of a pen type syringe. This drug delivery device 100 comprises a dose setting mechanism 102, a reservoir holder 104, and a removable cap 106. The reservoir holder 104 comprises a tubular member 101 that extends from a proximal end 105 to a distal end 112. The distal end 112 of the reservoir holder 104 comprises a coupling mechanism 108 for releasably coupling a dispense interface, such as a double ended needle.

The proximal end 105 of the reservoir holder 104 and the distal end 103 of the dose setting mechanism 102 are secured together. The pen type drug delivery device 100 may comprise a re-usable or a disposable pen type drug delivery device. Where the drug delivery device 100 comprises a re-usable device, the reservoir holder 104 and the dose setting mechanism 102 are removably coupled together. In a disposable device, they are permanently coupled together. The dose setting mechanism 102 comprises an outer housing 107 that extends from a proximal end 110 to a distal end 103 of the dose setting mechanism 102. In one preferred arrangement, the housing 107 contains a spindle or piston rod 109, such as a threaded spindle 109 that rotates when a dose is injected. The spindle or piston rod may urge a piston of a reservoir to be moved in distal direction for expelling a predetermined amount of a medicament or drug out of the reservoir.

To inject a previously set dose, a double ended needle assembly is attached to the coupling mechanism 108 provided at the distal end 112 of the tubular member 101 of the reservoir holder 104. Preferably, the distal end 103 of the holder comprises a thread 121 (or other suitable connecting mechanism such as a snap lock, snap fit, form fit, or bayonet lock mechanism) so that the needle assembly may be removably attached to the distal end 103 of the holder. When the drug delivery device 100 is not in use, the removable cap 106 can be releasably retained over the reservoir holder 104. An inner reservoir cavity 111 defined by the reservoir holder 104 is dimensioned and configured to securely receive and retain a reservoir 120.

Figure 2:
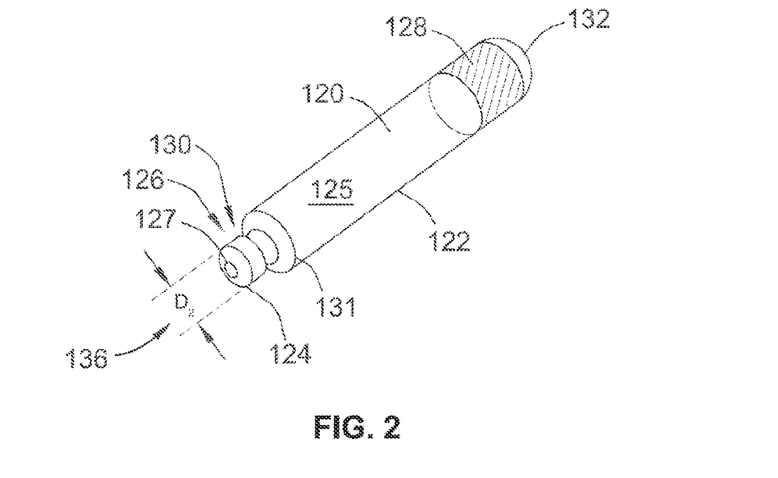
FIG. 2 illustrates a reservoir that may be loaded into a reservoir holder of the pen type drug delivery device illustrated in FIG. 1.

FIG. 2 illustrates a perspective view of the reservoir 120 that may be used with the drug delivery device 100 illustrated in FIG. 1. The reservoir 120 includes a generally tubular barrel 122 extending from a distal end 130 to a proximal end 132. The distal end 130 is defined by an inwardly converging shoulder 131.

At the distal end 130, the reservoir 120 includes a smaller diameter neck 126 and this neck 126 projects distally from the shoulder 131 of the barrel 122. Preferably, this smaller diameter neck 126 is provided with a large diameter annular bead (not shown) and this bead extends circumferentially thereabout at the extreme distal end 130 of the neck 126. A pierceable seal or septum 127 is securely mounted across the open distal end 130 defined by the neck 126. The seal 127 may be held in place by a metallic sleeve or ferrule 124. This ferrule 124 may be crimped around the circumferential bead at the distal end 130 of the neck 126. The medicament 125 is pre-filled into the reservoir 120 and is retained within the reservoir, in part, by the pierceable seal or septum 127, the metallic sleeve 124, and the stopper 128. The stopper 128 is in sliding fluid-tight engagement with the inner tubular wall of the barrel 122. Axially directed forces acting upon the stopper 128 during dose injection or dose administration urges the medication 125 from the reservoir through a double ended needle mounted onto the distal end 112 of the reservoir holder 104 and into the injection site. Such axial forces may be provided by the spindle 109.

A portion of the reservoir holder 104 defining the reservoir holder cavity 111 is of substantially uniform diameter represented in FIG. 1 by $D_1$ 134. This diameter $D_1$ 134 is preferably slightly greater than the diameter $D_2$ 136 of the reservoir 120. The interior of the reservoir holder 104 includes an inwardly-extending annual portion or stop that is dimensioned to prevent the reservoir 120 from moving within the reservoir holder 104. In this manner, when the reservoir 120 is loaded into the cavity 111 of the reservoir holder 104 and the reservoir holder 104 is then connected to the dose setting member 102, the reservoir 120 will be securely held within the reservoir cavity. More particularly, the neck 126 and ferrule 124 of the reservoir 120 are inserted in a proximal to distal direction into the open proximal end 105 of the reservoir holder 104 with the ferrule 124 eventually passing entirely into the holder 104. With the holder 104 removably coupled to the dose setting mechanism 102, the proximal end 132 of the reservoir 120 will typically abut a stop provided by the dose setting member 102.

A number of doses of a medicament 125 may be dispensed from the reservoir 120. Preferably, the reservoir 120 contains a type of medicament 125 that must be administered often, such as one or more times a day. One such medicament 125 is insulin. The stopper 128 is retained in a first end or proximal end 105 of the reservoir 120 and receives an axial force created by the spindle 109 of the dose setting mechanism 102.

The dose setting mechanism 102 further comprises a dose setter 117 at the proximal end 110 of the dose setting mechanism 102. In one exemplary arrangement, the dose setter 117 is rotated to set a dose. As the dose setter 117 is rotated, it moves in a helical fashion away from the proximal end 105 of the dose setting member 102. To administer this set dose, the user attaches the needle assembly comprising a double ended needle on the distal end 103 of the reservoir holder 104. In this manner, the needle assembly pierces the seal 127 of the reservoir 120 and is therefore in liquid communication with the medicament 125. The user pushes on the dose setter 117 to inject the set dose. The same dose setting and dose administration procedure is followed until the medicament 125 in the reservoir is expended, at which time a new reservoir may be loaded in the device if such a device comprises a re-usable drug delivery device 100. To exchange an empty reservoir, the user is called upon to remove the reservoir holder 104 from the dose setting mechanism 102. Where the device comprises a disposable drug delivery device 100, the device comprising the empty reservoir is disposed of and a new delivery device is obtained for subsequent dose administration.

Figure 3:
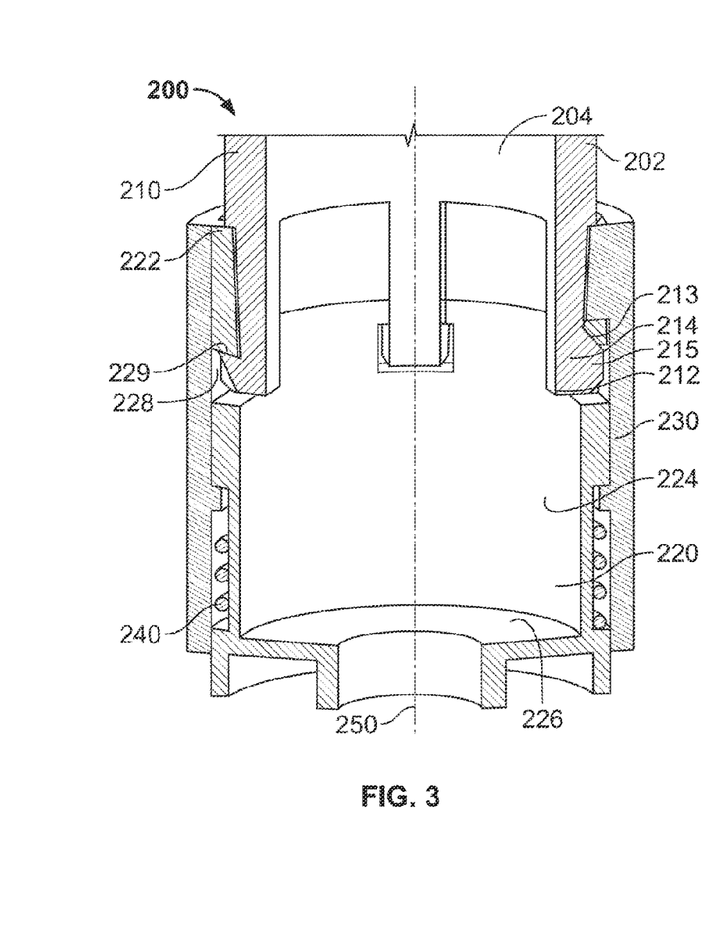
FIG. 3 illustrates a cross-sectional view of a first arrangement of a flexible fastener that may be used with a pen type drug delivery device, such as the drug delivery device illustrated in FIG. 1.

FIG. 3 illustrates a cross-sectional view of a first arrangement of a flexible fastening means or flexible fastener 200 that may be used with a pen type drug delivery device 100, such as the drug delivery device 100 illustrated in FIG. 1. In one preferred arrangement, this flexible fastener comprises a snap-fit comprising one or more flexible features 214, e.g. flexible arms. More specifically, FIG. 3 shows a proximal end 212 of a reservoir holder 210, a distal end 222 of a dose mechanism or dose setting mechanism 220, and a sleeve 230. The reservoir holder 210 shown in FIG. 3 is similar to the reservoir holder 104 of FIG. 1 but somewhat modified. For example, proximal end 212 of the reservoir holder 210 comprises at least one flexible feature 214. Reservoir holder 210 also comprises a cylindrically shaped main body 202 defining a centrally located aperture 204.

Flexible feature 214 may comprise a flange or an extension or protrusion 215 at the proximal end 212 of reservoir holder 210 and is configured such that, when pressure is applied to the exterior surface of the feature, feature 214 can move inwards, toward a center axis 250, shown in FIG. 3. Therefore, when a user presses or pushes against the feature 214, applying pressure in the direction toward the center axis 250, flexible feature 214 bends or flexes radially inward.

The dose mechanism 220 is also similar to the dose setting mechanism 102 of FIG. 1 but somewhat modified. Dose mechanism 220 comprises a cylindrically shaped main body 224 also defining a centrally located aperture 226. A spring 240 is situated within the aperture 226 such that it wraps around the circumference of the exterior surface of dose mechanism 220. Dose setting mechanism 220 comprises at least one corresponding opening 228. Flexible feature 214 form fits or snaps into opening 228 of dose mechanism 220. In this manner, and as explained in greater detail below, the feature can provide a fastening or locking feature for fastening the reservoir holder 210 to the dose setting mechanism 220.

In use, the proximal end 212 of reservoir holder 210 slides within aperture 226 of dose mechanism 220. Preferably, the aperture 226 of dose mechanism 220 has a diameter that is slightly larger than the diameter of aperture 204 of reservoir holder 210. As can be seen from FIG. 4, when flexible feature 214 contacts opening 228 of dose mechanism 220, flexible feature 214 slides through opening 228 and a retention feature 213 on flexible arm 214 contacts a corresponding retention feature 229 on dose mechanism 220. These retention features 213, 229 lie in (or nearly in) a transverse plane, so the angle of force applied to flexible feature 214 prevents it from being pulled out of opening 228 when reservoir holder 210 is pulled away from dose mechanism 220. Therefore, when extension 215 of flexible feature 214 is positioned through this opening 228, the reservoir is fastened to or retained within dose mechanism 220. In one arrangement, the flexible feature 214 may be configured and designed so as to provide an audible or tactile indication to the user of the device when the reservoir housing 107 has been successfully fastened to a correct dose setting mechanism 220.

As illustrated, sleeve 230 comprises a slidable sleeve and may be manually positioned so as to conceal at least a portion of the flexible feature 214. If sleeve 230 is positioned as illustrated in FIG. 3, then to disengage the flexible feature 214, the sleeve 230 is slid or moved axially in the proximal direction. This causes sleeve 230 to contact the angled face on flexible feature 214 and force it inwards, so that the retention feature 213 is disengaged and can be removed. In alternative embodiments, the sleeve 230 might need to be moved in other directions, for example axial, rotational, or helical, or in any combination of directions. Requiring a two-step process such as this for removal of the reservoir holder 210 from dose mechanism 220 reduces the risk of accidental disassembly.

Figure 4:
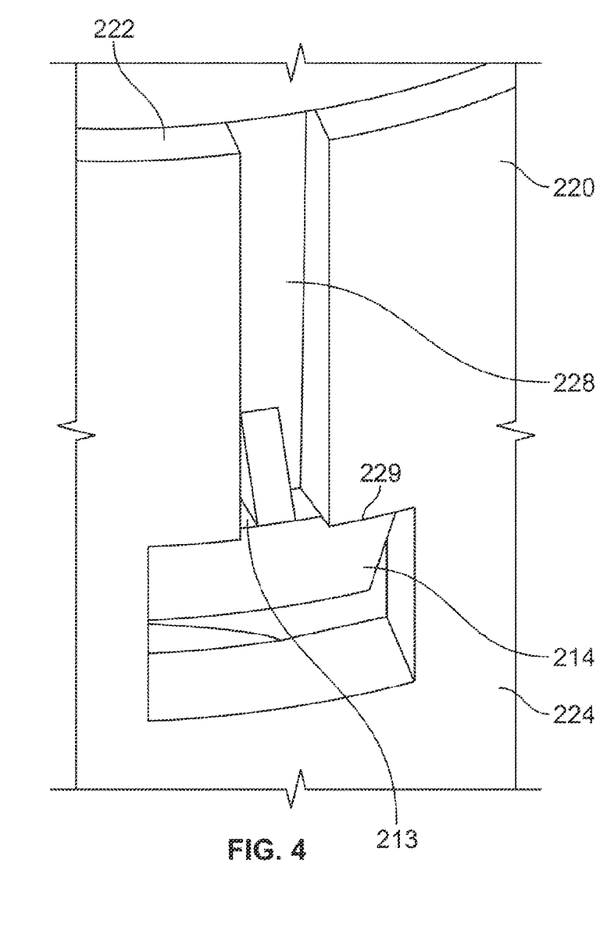
FIG. 4 illustrates an enlarged view of an exemplary slot that may be present in a device, such as the device shown in FIG. 3.

FIG. 4 illustrates an enlarged view of an exemplary opening 228 that may be present in dose mechanism 220, such as the mechanism shown in FIG. 3. As shown in FIG. 4, opening 228 may comprise a "T" shape, with an elongated opening 228 that extends axially through main body 224 and a more compact opening 228 that extends substantially perpendicular to the elongated opening 228. The elongated opening 228 may extend through the distal end 222 of dose mechanism 220. The "T" shape is made to correspond to flexible feature 214.

Figure 5:
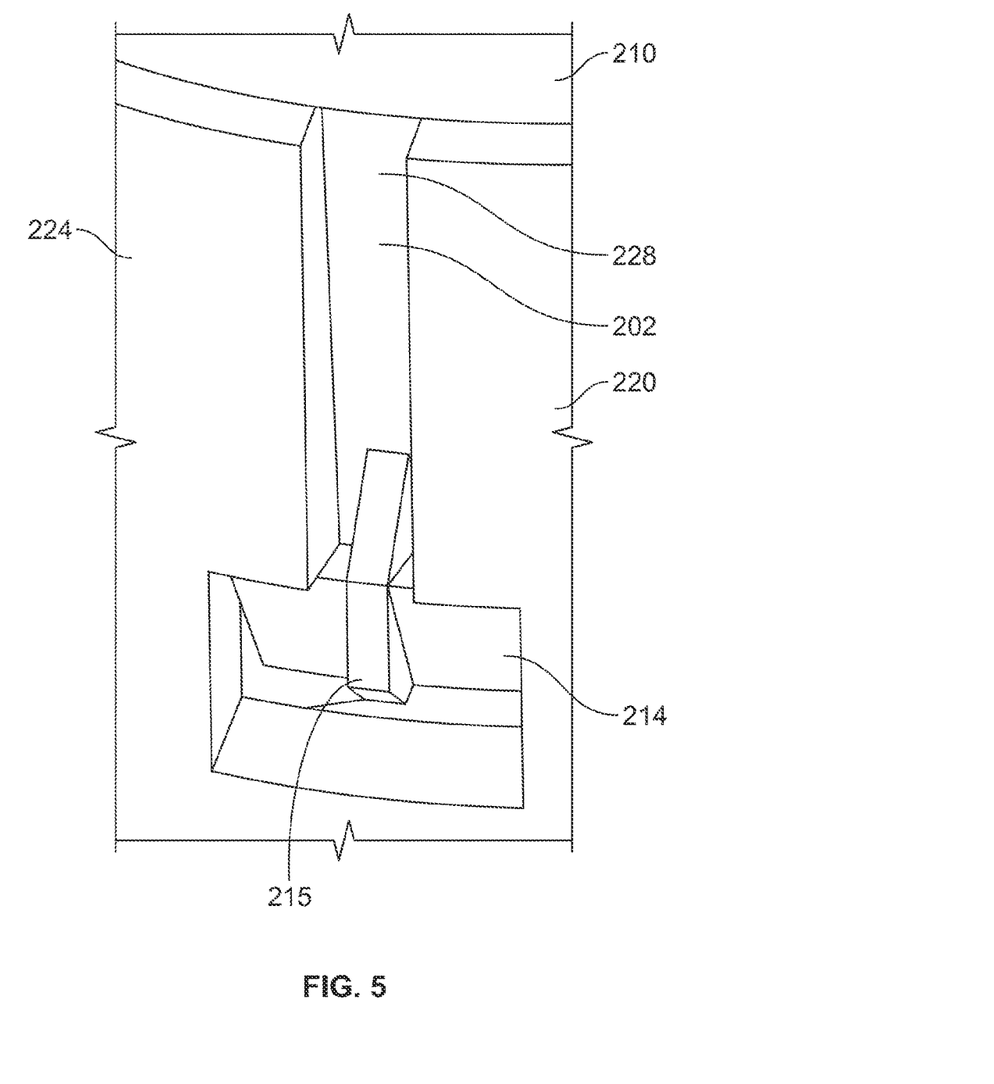
FIG. 5 illustrates an enlarged view of an exemplary orientation element that may be present in a reservoir, such as the reservoir shown in FIG. 3.

FIG. 5 illustrates an enlarged view of an exemplary flexible feature 214 from FIGS. 3 and 4. As illustrated, flexible feature 214 has an extension or a protrusion 215 in form of a center rib that extends orthogonally from main body 202. Center rib of protrusion 215 is used to aid orientation of flexible feature 214 within opening 228 during the insertion of reservoir holder 210 within dose mechanism 220. Center rib of protrusion 215 is shaped such that it will fit within the elongated portion of opening or aperture 228. In an alternative embodiment (not shown), the flexible feature 214 could be contained within dose mechanism 220, and opening 228 could be in reservoir holder 210. One advantage of such an arrangement is that the flexible parts would be protected from accidental damage.

Figure 6:
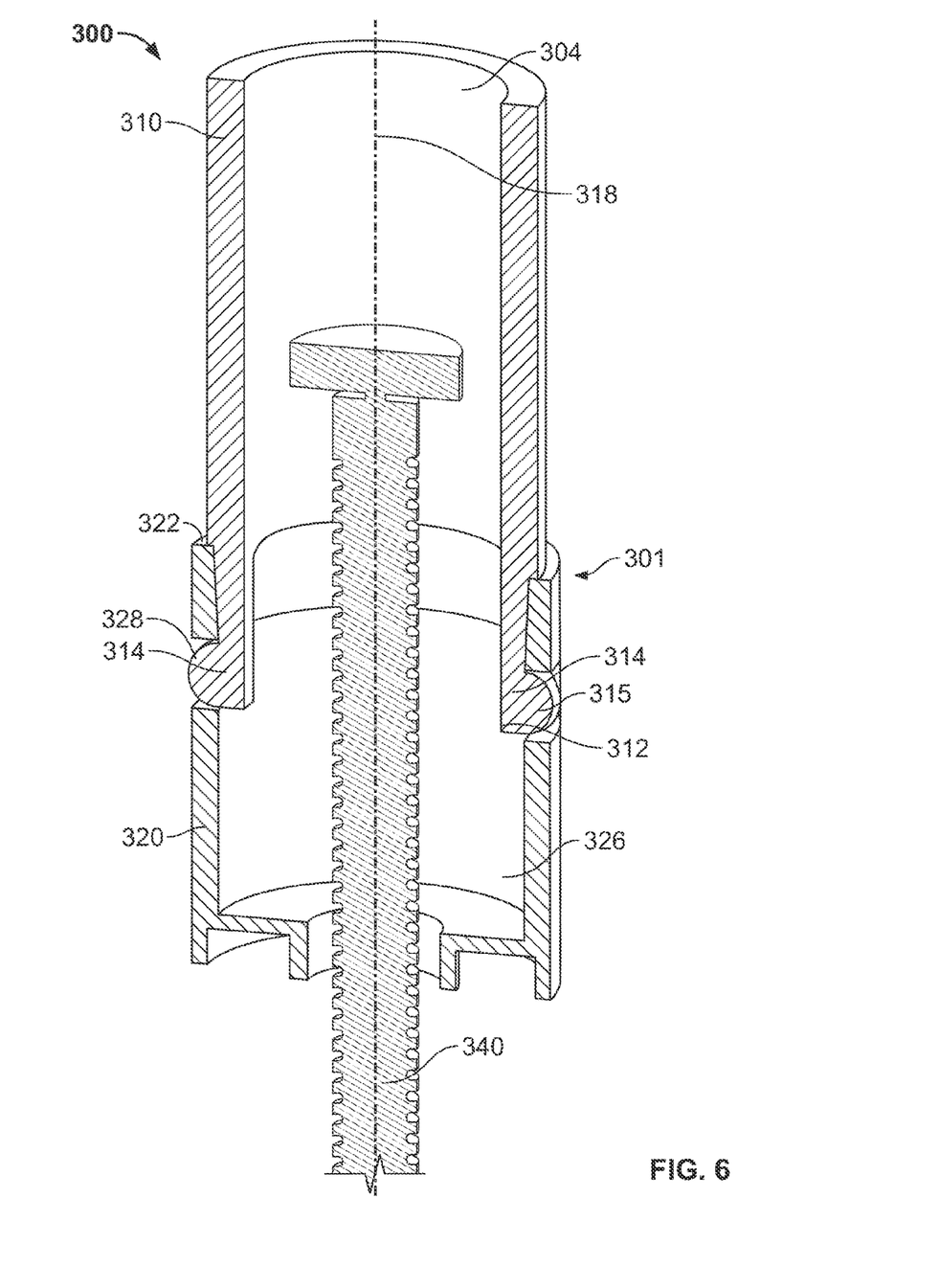
FIG. 6 illustrates a cross-sectional view of an alternative arrangement of a flexible fastener that may be used with a pen type drug delivery device, such as the drug delivery device illustrated in FIG. 1.

FIG. 6 illustrates a cross-sectional view of an alternative arrangement of a pen type drug delivery device 300, such as the drug delivery device 100 illustrated in FIG. 1. More specifically, FIG. 6 illustrates a drug delivery device 300 comprising an alternative flexible fastener 301. As illustrated, the device comprises a proximal end 312 of a reservoir holder 310 and a distal end 322 of a dose mechanism or dose setting mechanism 320. The reservoir holder 310 shown in FIG. 6 is similar to the reservoir holder 210 of FIG. 3. The dose mechanism 320 operates in a similar manner as the dose setting mechanism 320 of FIG. 3. FIG. 6 also shows a spindle 340 that extends through openings 304, 326 of reservoir holder 310 and dose mechanism 320. In one arrangement, the spindle 340 of the dose setting mechanism 320 may rotate during a dose administration step.

As was also present in FIG. 3, proximal end 312 of the reservoir holder 310 comprises a flexible fastener 301 comprising at least one flexible feature 314. Flexible feature 314 form fits or flexes into opening 328 of dose mechanism 320. In this manner, the flexible feature 314 can provide a fastening mechanism for fastening the reservoir holder 310 to the dose setting mechanism 320. Flexible feature 314 comprises a larger extension or protrusion 315 than flexible feature 214 of FIG. 3, so that this flexible feature 314 is easier to manipulate by a user. Flexible feature 314 is configured such that when pressure is applied to the exterior surface of the feature, snap feature 314 bends about axes in a transverse plane and move inwards, toward a center axis 318, shown in FIG. 6. Thus when a user presses or pushes against flexible feature 314, applying pressure in the direction toward central axis 318, flexible feature 314 flexes until the feature is no longer within opening 326 of dose mechanism 320. In alternative embodiments, however, flexible feature 314 may flex about any other axis, e.g., axial, radial, or helical.

Figure 7A:
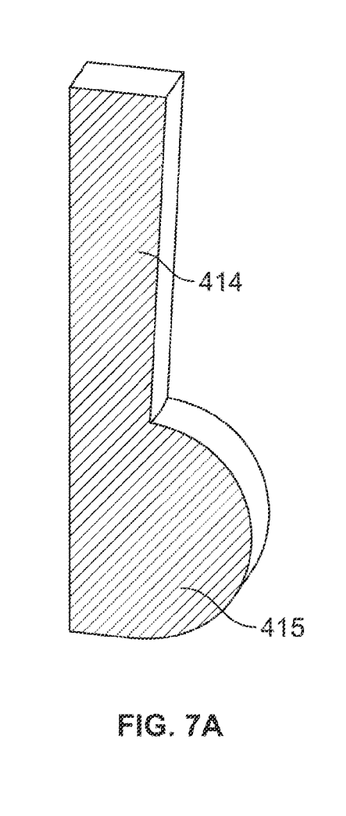
FIGS. 7a-b illustrate exemplary profiles for the flexible fastener in FIG. 6.
Figure 7B:
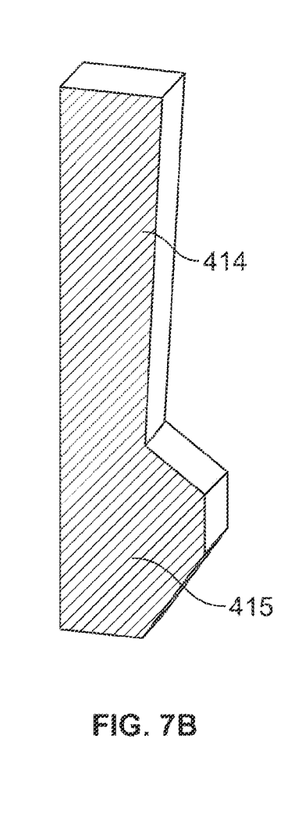

FIGS. 7*a* and 7*b* illustrate exemplary profiles for flexible features shown in FIG. 6. As can be seen in these profiles, the profile for an extension 415 of a feature 414 may be rounded or angular. For example, the exemplary rounded profile illustrated in FIG. 7*a* provides for equal force required for assembly and disassembly. And the angular profile illustrated in FIG. 7*b* allows for easier assembly, as less force is required, but more difficult disassembly, as more force is required to remove the snap feature. If a reservoir holder 310 (shown in FIG. 6) has multiple flexible features 314, each flexible feature 314 may be identical, or alternatively, the flexible features 314 may comprise different sizes or shapes.

It is also conceivable that a flexible feature 314 or 414 provides a coding functionality. This means, the shape of the flexible feature 314 or 414 or the shape and profile of an extension 415 may be designed so as to code a corresponding reservoir or reservoir holder or a corresponding dose setting mechanism 220, 320. Only predetermined and specified reservoirs or reservoir holders may then be used with corresponding dose setting mechanisms, since wrong reservoirs or reservoir holders or wrong dose setting mechanisms do not match together. This may prevent unwanted cross use. Any combination of any embodiment of a flexible fastener disclosed herein may comprise such coding functionality.

Figure 8:
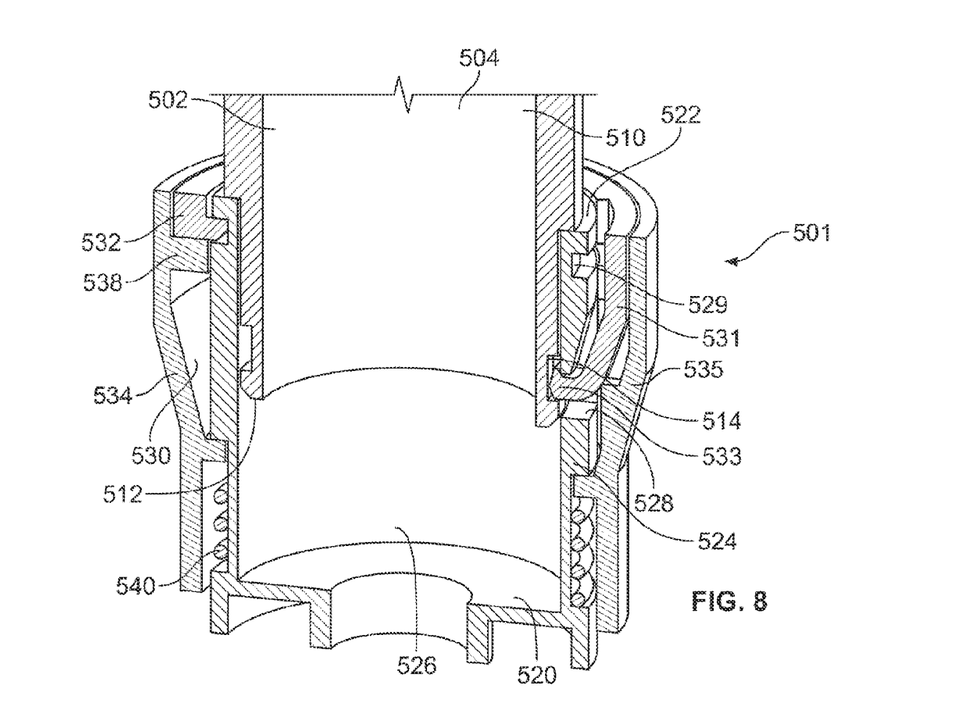
FIG. 8 illustrates a cross-sectional view of an alternative arrangement of a flexible fastener that may be used with a pen type drug delivery device, such as the drug delivery device illustrated in FIG. 1.

FIG. 8 illustrates a cross-sectional view of an alternative arrangement of a flexible fastener 501 that may be used with a pen type drug delivery device 300, such as the drug delivery device 100 illustrated in FIG. 1. More specifically, FIG. 8 shows a proximal end 512 of a reservoir holder 510, a distal end 522 of a dose mechanism or dose setting mechanism 520, a sleeve 530, and a fastening or retention ring 532. The reservoir holder 510 shown in FIG. 8 is similar to the reservoir holder 104 of FIG. 1 somewhat modified. Reservoir holder 510 comprises a cylindrically shaped main body 502 defining a centrally located aperture 504. Proximal end 512 of the reservoir holder 510 comprises a groove 514 along the exterior surface of the holder.

The dose mechanism 520 is also similar to the dose setting mechanism 102 of FIG. 1 but somewhat modified. Dose mechanism 520 comprises a cylindrically shaped main body 524 also defining a centrally located aperture 526. A spring 540 is configured so as to wrap around the circumference of the exterior surface of dose mechanism 520. Dose mechanism 520 comprises an opening 528 and a dose mechanism groove 529. Dose mechanism groove 529 may extend along the entire circumference of the exterior of main body 524.

Sleeve 530 comprises a generally cylindrically shaped main body 534 with an engaging rib 535. Interior shelves 538 extend orthogonally from the interior of main body 534.

Figure 9:
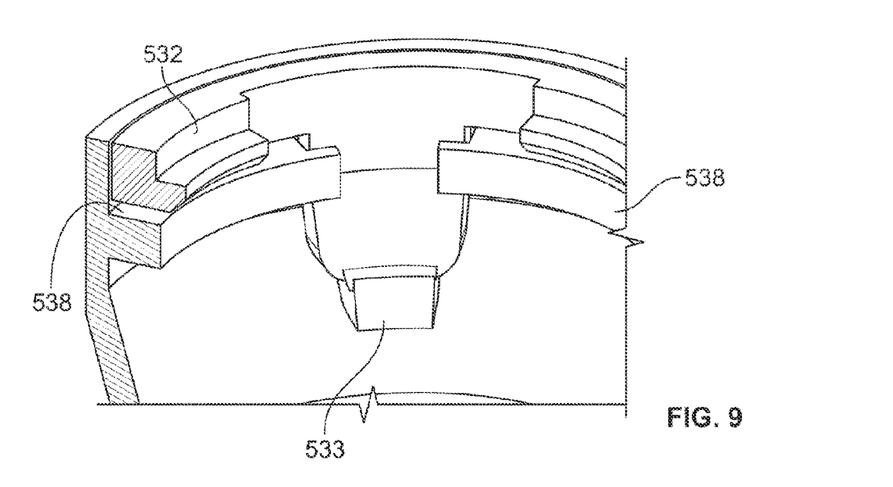
FIG. 9 illustrates an enlarged view of a portion of the interior of sleeve with flexible fastener from FIG. 8.

A fastening ring 532 comprises an extension 531 that fits within dose mechanism groove 529. Fastening ring 532 also comprises a flexible fastening arm 533. FIG. 9 is an enlarged view of a portion of the interior of sleeve 530 with fastening ring 532 from FIG. 8.

Fastening arm 533 form fits or flexes into groove 514 of reservoir holder 510. In this manner, the fastening arm 533 can provide a locking or retention feature 213, 229. When sleeve 530 slides over dose mechanism 520 in the distal direction, the top surfaces of shelves 538 engage fastening ring 532, as shown in FIGS. 8 and 9. Engaging rib 535 then presses the flexible fastening arm 533 through opening 528 and into groove 514 of reservoir holder 510, and maintains arm 533 in the position shown in FIG. 8.

Figure 10:
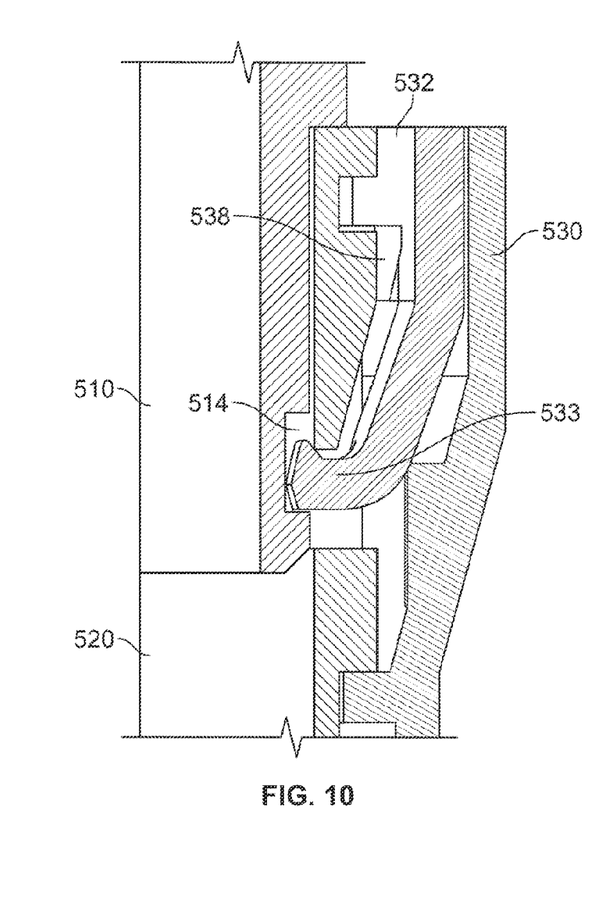
FIG. 10 illustrates an enlarged view of a portion of FIG. 8 in the fastened or locked position.
Figure 11:
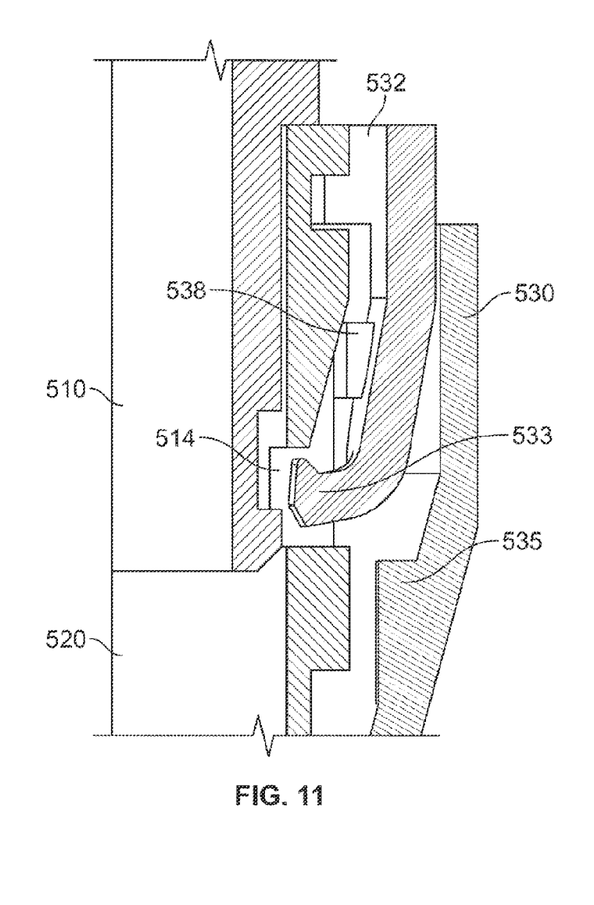
FIG. 11 illustrates an enlarged view of a portion of FIG. 8 in the unfastened or unlocked position.

Sleeve 530 may later be displaced in the proximal direction over dose mechanism 520, at which point a disengaging portion or arm of shelve 538 press against the interior surface of the fastening arm 533, forcing fastening arm 533 from the locked or retention position shown in FIG. 10 to the unlocked or released position shown in FIG. 11. The spring force to retain sleeve 530 in its retained position may be provided by the fastening arm 533 rather than a separate spring 540.

Figure 12:
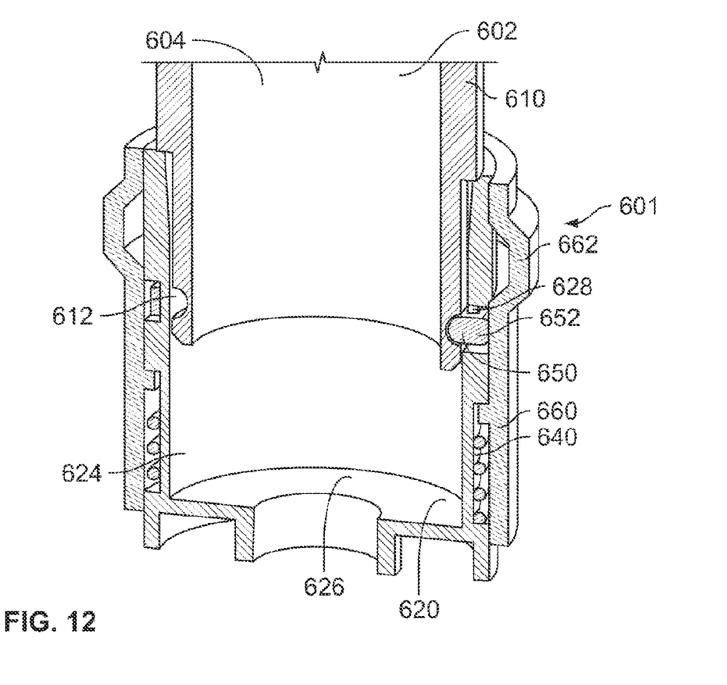
FIG. 12 illustrates a cross-sectional side view of an alternative arrangement of a drug delivery device, such as the drug delivery device illustrated in FIG. 1.

FIG. 12 illustrates a cross-sectional view of an alternative arrangement of a flexible fastener 601 that may be used with a pen type drug delivery device 300, such as the drug delivery device 100 illustrated in FIG. 1. This flexible fastener 601 arrangement allows for fastening of a reservoir holder 610 to dose setting mechanism 620 using a fastening ring 650.

The dose mechanism or dose setting mechanism 620 is similar to the dose setting mechanism 102 of FIG. 1 but somewhat modified. Dose setting mechanism 620 comprises a cylindrically shaped main body 624 defining a centrally located aperture 626. A spring 640 is configured so as to wrap around the circumference of the exterior surface of dose mechanism 620. Dose mechanism 620 comprises at least one corresponding opening 628.

The reservoir holder 610 shown in FIG. 12 is similar to the reservoir holder 104 of FIG. 1 but somewhat modified. Reservoir holder 610 comprises a cylindrically shaped main body 602 defining a centrally located aperture 604, as well as a groove 612.

Figure 13:
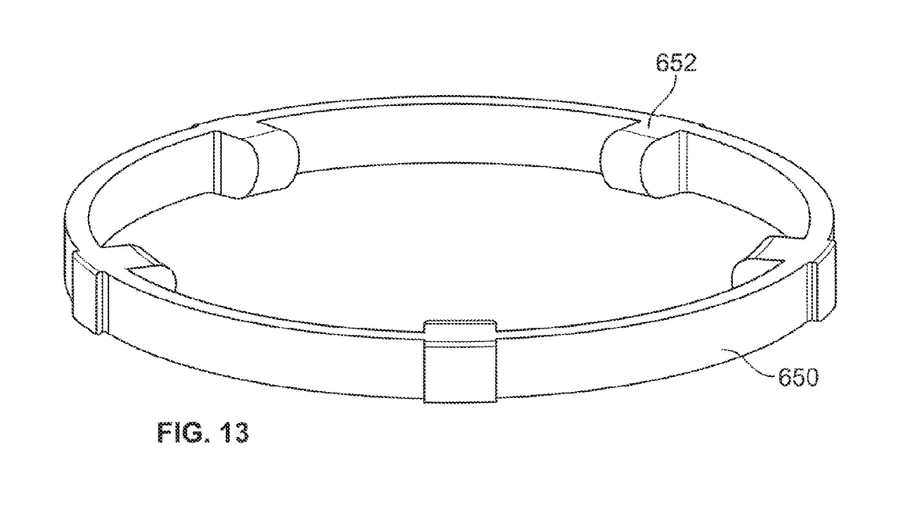
FIG. 13 illustrates an exemplary flexible ring that may be used with the device shown in FIG. 12.

As shown in FIG. 13, fastening ring 650 comprises a plurality of radial protrusions 652. Radial protrusions 652 extend toward the center of fastening ring 650. Ring 650 comprises a circular shape, and preferably is made from a flexible material, for example a polymer such as PA, PP, POM, or HDPE. In an alternative embodiment, fastening ring 650 may be split or may comprise more than one component part. Such a multi-component fastening ring 650 arrangement may tend to increase flexibility and could also aid in assembly of the drug delivery device 300. The profile of fastening ring 650 may comprise various shapes and sizes to vary assembly and disassembly forces required by a user. In another alternative embodiment, fastening ring 650 may be replaced by ball bearings. One advantage of using the fastening ring 650 is that the ring prevents the reservoir holder 610 from unwanted removal.

Figure 14:
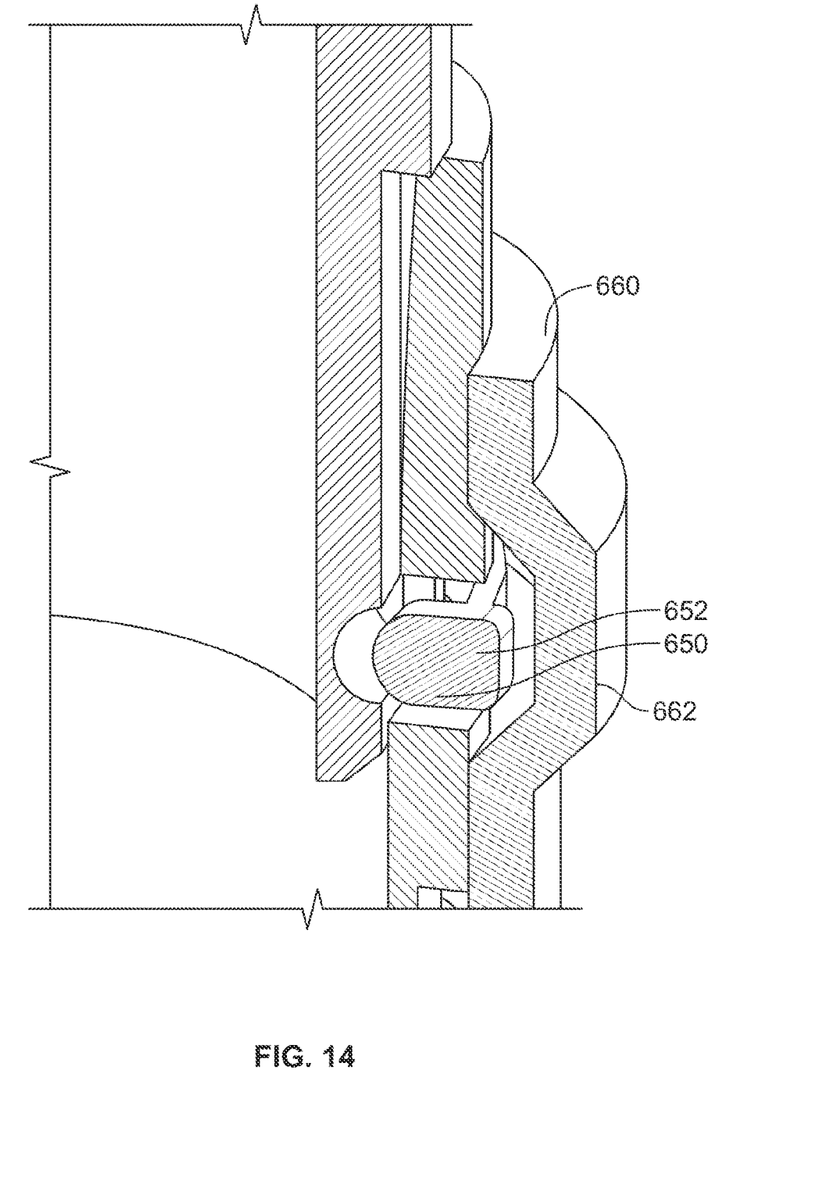
FIG. 14 illustrates an enlarged view of the drug delivery device of FIG. 12, in the unfastened or unlocked position.

FIG. 12 shows the assembly in its locked position, in which the reservoir holder 610 is retained. Radial protrusions 652 of the fastening ring 650 pass through openings 628 and fit into groove 612. In this illustrated arrangement, even if the reservoir holder 610 is pulled away from the dose mechanism 620, the sidewall of the sleeve 660 prevents movement of the radial protrusions 652, and hence the reservoir holder 610 is retained. When a sleeve 660 is displaced in the proximal direction and reservoir holder 610 is simultaneously pulled away from dose mechanism 620, the radial protrusions 652 flex outwardly and are thereby pushed out of or removed from the groove 612 and consequently into a corresponding plurality of pockets 662 in sleeve 660, allowing for removal of reservoir holder 610 or a reservoir assembly. This unlocked position is shown in FIG. 14.

Those of skill in the art will recognize alternative geometries. For example, changing materials, varying the length, width, depth, or profile shape of the snap features may vary the force required for assembly, disassembly, or any tactile feedback.

The proposed flexible fasteners may apply to any drug delivery device, with any type of reservoir such as a molded reservoir or primary pack, e.g. inhaler, pouch. The proposed snap-fit fasteners may also comprise a coding method to the reservoir holder 610 to prevent insertion of a reservoir into the incorrect holder. For example, axial assembly of the reservoir holder 610 into the device allows for axial coding, which gives much more space and hence many more combinations than would be possible with a bayonet fastening.

The proposed fastener results in a number of advantages. For example, it is easier for many users to fasten and unfasten the reservoir assembly using an axial motion rather than a twisting motion. The proposed fastener helps to ensure that a delivery device can only be used with a medicament 125 for which the device is intended. The fastener also aids in allowing a reservoir holder 610 to only be fastened to a correct dose setting member while also preventing a user from fastening the reservoir holder 610 to an incorrect dose setting member.

Exemplary embodiments of the present disclosure have been described. Those skilled in the art will understand, however, that changes and modifications may be made to these arrangements without departing from the true scope and spirit of the present disclosure, which is defined by the claims.

The disclosure is not limited to specific embodiments but comprises any combination of elements and aspects of different embodiments. Moreover, the disclosure comprises any combination of claims and any combination of features disclosed by the claims.

The invention claimed is:
1. An assembly comprising,
a cylindrically shaped reservoir holder configured to accept a reservoir containing a medicament;
a dose setting mechanism comprising an outer housing and configured to allow a user of the assembly to set a dose of the medicament for delivery from the reservoir; and
a retention ring comprising a flexible feature that is configured to bend radially, where the retention ring is configured as a separate component that is connected to and engaged with the outer housing of the dose setting mechanism and is configured to fasten the reservoir holder to the dose setting mechanism through engagement of a retention feature located on the flexible feature with a separate corresponding retention feature located on the reservoir holder, where engagement of the flexible feature with the separate corresponding retention feature forms a connection that prevents the flexible feature from disengaging from the separate corresponding retention feature, where the flexible feature is configured with a shape and profile to code a corresponding reservoir or a corresponding reservoir holder or a corresponding dose setting mechanism to prevent loading of the reservoir holder or the reservoir with an incorrect drug type into a drug delivery device.

2. The assembly of claim 1, wherein the flexible feature comprises at least one flexible arm bendable for connecting or disconnecting the reservoir holder with or from the dose setting mechanism.

3. The assembly of claim 1, wherein the retention ring bends radially when connecting and disconnecting the reservoir holder with or from the dose setting mechanism.

4. The assembly of claim 1, wherein the flexible feature of the reservoir holder and the dose setting mechanism comprises at least one protrusion for engaging at least one aperture provided near a distal end of the corresponding reservoir holder and the corresponding dose setting mechanism.

5. The assembly of claim 1, comprising a sleeve configured to be axially movable and to interact with the flexible feature for connecting or disconnecting the reservoir holder with or from the dose setting mechanism.

6. The assembly of claim 5, wherein said sleeve is movable from a first axial position to a second axial position so as to prevent the reservoir holder to be disconnected from the dose setting mechanism in the first axial position of the sleeve and to allow the reservoir holder to be disconnected from the dose setting mechanism in the second axial position of the sleeve.

7. The assembly of claim 5, wherein the sleeve conceals at least a portion of the flexible feature when the reservoir holder is connected to the dose setting mechanism.

8. The assembly of claim 1, wherein the reservoir holder comprises a tubular member, said tubular member extending from a distal end to a proximal end of the reservoir holder and defining an inner cavity that is dimensioned to receive the reservoir.

9. The assembly of claim 8, wherein a first coupling mechanism is provided at said distal end of said tubular member, said first coupling mechanism configured for releasably coupling a dispense interface to the reservoir holder.

10. A The assembly of claim 1, wherein the drug delivery device comprises:
   a dose setting means for setting dose of a drug to be dispensed, and
   a piston rod, wherein after said dose has been set, said piston rod can be rotated to dispense said dose.

* * * * *